(12) United States Patent
Jansen et al.

(10) Patent No.: US 6,437,016 B2
(45) Date of Patent: *Aug. 20, 2002

(54) RADIATION-CURABLE COMPOUND DERIVED FROM A HYDROXYALKYLAMIDE

(75) Inventors: Johan F. G. A. Jansen, Geleen; Aylvin J. A. A. Dias, Maastricht; Pascal M. H. P. Tijssen, Beek, all of (NL)

(73) Assignee: DSM N.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/755,134

(22) Filed: Jan. 8, 2001

Related U.S. Application Data

(63) Continuation of application No. PCT/NL99/00407, filed on Jun. 30, 1998.

(30) Foreign Application Priority Data

Jul. 6, 1998 (EP) .............................. 98202237

(51) Int. Cl.$^7$ ........................ C07C 235/08; C08F 20/36; C08F 2/46
(52) U.S. Cl. ........................ 522/175; 522/173; 560/115; 560/205; 560/215
(58) Field of Search ................................ 522/167, 173, 522/175; 560/215, 205, 196, 127, 128, 115

(56) References Cited

U.S. PATENT DOCUMENTS

| | | | |
|---|---|---|---|
| 3,366,613 A | | 1/1968 | Kelley |
| 3,928,499 A | * | 12/1975 | Tomalia et al. |
| 4,788,328 A | | 11/1988 | Goel et al. |
| 5,730,966 A | * | 3/1998 | Torgerson et al. |
| 6,245,829 B1 | * | 6/2001 | Meij et al. |

FOREIGN PATENT DOCUMENTS

| | | |
|---|---|---|
| DE | 37 10 279 | 10/1988 |
| DE | 39 13 939 | 1/1991 |

* cited by examiner

*Primary Examiner*—Susan W. Berman
(74) *Attorney, Agent, or Firm*—Pillsbury Winthrop LLP

(57) ABSTRACT

The invention relates to a radiation curable compound being a mono or multi valent carboxylic ester of a compound containing a hydroxyalkylamidegroup and a hydroxygroup in which the carboxylic ester is derived from an α,β-ethylenically unsaturated carboxylic acid.

A coating composition comprising this compound has a high rate of polymerisation and shows the desired chemical and mechanical properties.

9 Claims, No Drawings

RADIATION-CURABLE COMPOUND DERIVED FROM A HYDROXYALKYLAMIDE

This application is a continuation of application Ser. No. PCT/NL99/00407, filed Jun. 30, 1999.

The invention relates to a radiation-curable compound and a composition comprising this compound.

During radiation curing processes the transformation of the fluid applied film to a solid crosslinked network can be considered to progress through three distinct stages being induction, polymerisation and attainment of maximum cure plateau. (Chemistry and Technology of UV and EB formulations, Volume IV, Oldring, 1991, pages 8–12).

Factors which improve or inhibit cure rate are, for example, the lamp system (UV-dose, intensity, wavelength, IR-content) and the chemical system (reactivity, absorption, coating weight, pigmentation, temperature, oxygen inhibition and substrate).

For commercial coating operations, it is necessary that the coating achieves a tackfree surface within seconds or less, because the interval between application of the coating and stacking or rewinding of the coated substrate is very short. Failure of the coating to achieve a non-tacky surface in this brief interval will result in the layers of coated substrate (in a stack or roll) sticking together ("blocking").

It is the object of the present invention to provide a coating composition having a high cure rate or rate of polymerisation and having the desired chemical and mechanical properies.

The radiation curable compound according to the invention is a mono or multi valent carboxylic ester of a compound containing a hydroxyalkylamidegroup and a hydroxygroup in which the carboxylic ester is derived from an α,β-ethylenically unsaturated carboxylic acid.

A radiation curable composition comprising the compound according to the invention results in high maximum polymerization rates.

According to a preferred embodiment of the invention the compound is a compound according to formula (I):

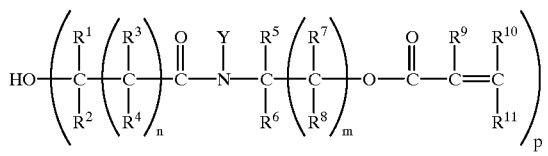

(I)

where:
Y=hydrogen, an $(C_1–C_8)$ alkyl group or

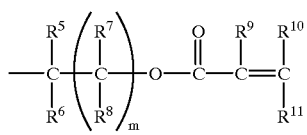

(II)

$R^1$, $R^2$, $R^3$, $R^4$, $R^5$, $R^6$, $R^7$, $R^8$ are, identical or different, hydrogen or a lineair, branched or cyclic $(C_1–C_8)$ alkyl chain, $R^9$=hydrogen, $(C_1–C_5)$alkyl, —$CH_2OH$ or $CH_2COOX$, $R^{10}$, $R^{11}$=hydrogen, $(C_1–C_8)$ alkyl, $(C_6–C_{10})$aryl or COOX, X=hydrogen or $(C_1–C_8)$ alkyl,
m=1–10,
p=1–4 and
n=1–10

$R^1$, $R^2$ or $R^3$ may form part of a cycloalkyl group.

Preferably n=1–4.

Because of the resulting excellent reactivity characteristics m is preferably 1–4.

Preferably, p is 1 or 2

Preferably, Y is hydrogen.

Preferably, $R^1$, $R^2$, $R^3$, $R^4$, $R^5$, $R^6$, $R^7$ and $R^8$ are hydrogen or methyl.

$R^9$ is preferably hydrogen or (m)ethyl.

$R^{10}$ and $R^{11}$ are preferably hydrogen.

The compound can be obtained, for instance, by an esterification reaction between a hydroxy functional hydroxyalkylamide and an unsaturated carboxylic acid, at a temperature between, for example, 80° C. and 140° C.

Preferably, 1–1.5 mol of acid are used per mole of hydroxide.

Preferably, the reaction takes place in the presence of an organic solvent, such as, for example, xylene, toluene or tetrahydrofuran.

Preferably, the reaction takes place in the presence of a stabilizing compound which prevents polymerization of the unsaturated ester groups under the conditions used for effecting this reaction. The stabilising compound or a mixture of stabilising compounds is generally used in amounts between about 50 and about 2000 ppm and preferably between 75 and 1000 ppm. They can be used in aerobic or anaerobic conditions depending on the stabilising compound.

Suitable stabilizing compounds include, for example, hydroquinone, monomethylhydroquinone, anthraquinone, β-nitrostyrene, phenothiazine and 2,6-di-tert-butyl-4-methyl-phenol (BHT).

The esterification reaction may take place in the presence of a catalyst. Suitable catalysts include strong acids, for example, sulphur-containing organic acids like alkane sulphonic acids and methane sulphonic acid.

Suitable unsaturated carboxylic acids include, for example, (meth)acrylic acid and derivatives, crotonic acid, (semi-ester of) itaconic acid, maleic acid, citraconic acid, mesaconic acid and fumaric acid.

Preferably (meth)acrylic acid is applied.

The compound applied in the invention can also be obtained by the reaction between a hydroxy functional hydroxyalkylamide and an unsaturated carboxylic acid chloride, anhydride or ester.

Preferably, the reaction between the amide and the unsaturated chloride or anhydride takes place at temperatures between 0° C. and 30° C. in a solvent in the presence of a base. Suitable solvents include, for example, tetrahydrofuran, dichloromethane and diethylether. Suitable bases include, for example, pyridine and triethylamine.

Suitable chlorides, anhydrides or esters include the chlorides, anhydrides and esters of the in the foregoing mentioned carboxylic acids.

Preferably, the reaction between the amide and the unsaturated ester takes place at temperatures between 80° C. and 140° C. in the presence of a Lewis acid. Preferably, an excess of the unsaturated ester is applied. The ester functions both as solvent and as reactant. Suitable Lewis acids are, for example, tetra alkyl titanate and sulphuric acid.

According to a preferred embodiment of the invention the preparation of the compound according to the invention takes place by reaction between a hydroxy functional oxazoline and an unsaturated carboxylic acid.

Such a reaction can, for example, take place at a temperature between 50° C. and 140° C.

Suitable hydroxy functional oxazolines include, for instance, hydroxy functional ($C_1$–$C_{20}$) alkyloxazolines, for instance, β-hydroxy ethyl oxazoline and Ω-hydroxy undecyloxazoline.

Suitable unsaturated carboxylic acids include, for example, (meth)acrylic acid and derivatives, crotonic acid, (semi-ester of) itaconic acid, maleic acid, citraconic acid, mesaconic acid and fumaric acid. Preferably, (meth)acrylic acid is used.

Preferably the hydroxy functional oxazolines are prepared from, for instance, a lactone and an ethanolamine or 2-propanolamine. Suitable lactones are for instance propiolactone, butyrolactone, valerolactone and caprolactone.

An advantage of the hydroxy functional compound according to the invention is that the hydroxy group gives the possibility for attaching this compounds to a polymer. A suitable method to obtain the attachment is to react first the hydroxyl functional compound with a diisocyanate and to react subsequent with an hydroxy functional polymer. Suitable diisocyanates are, for example, toluene diisocyanate, hexane diisocyanate, isophorone diisocyanate or 3,4-isocyanate methyl-1-methyl cyclohexyl isocyanate (IMCI). Suitable hydroxy functional polymers are, for example, hydroxy functional polyethylene, polypropylene, polyester, poly(meth)acrylate, polyamide, polyether, polyisobutylene, polyacrylonitrile, polyurethane and polylactone.

Additives can also be connected via the hydroxy functionality of the hydroxy functional compound according to the present invention.

Suitable additives include for example, adhesion promoters, disperging agents, photo initiators and synergists.

The compound according to the invention can be cured by means of a free-radical reaction. In these reactions the free radicals can be obtained by radiation initiation.

Radiation-curing preferably takes place by means of, for example, a photochemical process such as, for example, ultraviolet radiation (UV) or a radiation-chemical process such as electron beam (EB).

UV and EB radiation are explained in greater detail by for example Bett et al. in the article entitled "UV and EB curing" (Jocca 1990 (11), pages 446–453).

The amount of the compound according to the invention can range between 0,01% by weight and 100% by weight in a composition according to the invention.

Generally, the radiation curable composition according to the invention is substantially solvent free.

The composition according to the invention can be used, for example, in coating compositions, inks and adhesives.

If desired and depending on the application, the compound can be combined with oligomers or polymers which are based, for example, on (meth)acrylate units, maleate units, fumarate units, itaconate units, vinylester units, vinylamide units and/or vinylether units.

Due to the relatively high cure speeds the present compounds can also be applied as additives for enhancing the cure speed of a formulation. In general such additives are used in amounts ranging between 0,01% and 25% by weight and preferably in amounts between 0,5% and 10% by weight relatively to the total amount of all ingredients.

After curing, the coatings according to the invention have many desired properties such as for example good chemical properties (resistance to solvents, acids, alkali and moisture), good optical properties and appearance, good mechanical properties (such as hardness, flexibility, adhesion, abrasion resistance, strength and durability), good thermal stability and good weatherability.

The composition comprising the radiation curable binder composition may further comprise pigments, stabilisers and other additives.

The radiation curable formulation generally consists of a prepolymer, a reactive diluent and additives. Two other possible components, depending upon the type of formulation and cure mechanism are pigments and photoinitiator system.

The compound according to the invention can for example be applied in a water based coating composition, in a solvent based coating composition, in a high solids coating composition, in a 100% solids coating composition and in a powder paint composition.

The most preferred irradiation source is ultraviolet light. Ultraviolet light is preferably high intensity light to provide a dosage to achieve reasonable curing rates. In the event that lower energy light is to be applied, it may then be desired to subject the compositions also to elevated temperatures in order to reduce the time for adequate polymerization to occur.

With respect to UV curing equipment we refer to, for example, pages 161–234 of Chemistry and Technology of UV and EB-formulations, Volume 1, Oldring, 1991.

Suitable lamps employed to provide the desired high intensity and availability of wavelength and spectral distribution include for example that available from Fusion Systems, Corp.

A composition according to the present invention can be applied on substrates such as, for example, plastic, paper, board, leather, glass, wood and metal.

This composition is preferably polymerised in the presence of a photoinitiator but it is also possible to polymerise in the absence of a photoinitiator.

Suitable photoinitiators allow for initiation of the curing process with exposure to light having wavelengths between about 200 nm and about 600 nm. Suitable photoinitiators have ketone functionalities and can be aromatic such as, for example, benzophenone. Darocur 1173® (Ciba) is a suitable benzyl-ketal-based photoinitiator, which contains 2-hydroxy-2-methyl-1-phenylpropane-1-one as an active component. Irgacure 184® (Ciba) is an aryl ketone containing hydroxycyclohexyl phenyl ketone as active component, and is a suitable photoinitiator. Irgacure 369® (active component 2-benzyl-2-dimethylaminol-1-(4-morpholinophenyl)-butanone-1) is also suitable. Acyl phosphines, such as for example 2,4,6,-trimethylbenzoyl diphenyl phosphone oxide (Lucerine TPO®, BASF) can also be used, as can Quantacure CPTX® (Octel Chemicals), which contains 1-chloro-4-propoxy thioxanthone as active component. Chemical derivatives of these photoinitiators are suitable, as are mixtures of these photoinitiators. A suitable combination of photoinitiators is Irgacure 1800™ (Ciba) consisting of 75% by weight Irgacure 184™ and 25% by weight (bis-(2,6-dimethoxy benzoyl)-2,4,4-trimethylpentyl fosfine oxide). Other suitable photoinitiators can be of the Norrish-II-type, for example, the combinations benzophenone with amine, maleimide with amine, thioxanthone with amine and antrachinon with amine.

The invention is explained by reference to the following non-restrictive examples.

In the following the cure behaviour is monitored with "real time infra red spectroscopy". The conversion of the double bonds during the photopolymerisation was monitored by means of infrared (Bruker IFS55).

EXAMPLE I

Synthesis of β-hydroxy-(N-ethyl-2-acryloyloxy) propionamide a) Synthesis of β-hydroxy-(N-ethyl-2-hydroxy) propionamide 61 grams of ethanol amine were slowly added to 72 grams of propiolactone under nitrogen at 80° C. during which the reaction temperature raised to 120° C. After the addition the reaction temperature was maintained at 120° C. for 2 hours. Subsequent cooling yielded β-hydroxy-(N-ethyl-2-hydroxy) propionamide in almost quantitative yields.

b) Synthesis of β-hydroxy-ethyl oxazoline 2 ml tetra butyl titanate (TBT) were added to 133 grams β-hydroxy-(N-ethyl-2-hydroxy) propionamide prepared above. The reaction mixture was heated to 240° C. for 2 hours. Subsequently the reaction mixture was distilled under reduced pressure yielding β-hydroxy-ethyl oxazoline in approximately 75% yield.

c) Synthesis of β-hydroxy-(N-ethyl-2-acryloyloxy) propionamide 15 grams of acrylic acid were added slowly at 62° C. to 10 grams of β-hydroxy-ethyl oxazoline, bubbling dry air through the liquid while maintaining the temperature below 90° C. After the addition the reaction temperature was raised to 90° C. and the reaction mixture was stirred for 3 hours at this temperature. After cooling to roomtemperature the reaction mixture was poured into chlorofom, washed thrice with a saturated sodium carbonate solution and once with a saturated sodium chloride solution. After evaporation of the chloroform under reduced pressure β-hydroxy-(N-ethyl-2-acryloyloxy) propionamide was obtained in approximately 80% yield.

EXAMPLE II

Synthesis of γ-hydroxy -(N-ethyl-2-acryloyloxy) butyramide a) Synthesis of γ-hydroxy-(N-ethyl-2-hydroxy) butyramide To 86 grams of butyrolactone under nitrogen at 80° C. were slowly added 61 grams of ethanol amine during which the reaction temperature raised to 120° C. After the addition the reaction temperature was maintained at 120° C. for 2 hours. Subsequent cooling yielded γ-hydroxy-(N-ethyl-2-hydroxy) butyramide in almost quantitative yields.

b) Synthesis of γ-hydroxy-propyl oxazoline 2 ml TBT were added to 147 grams of γ-hydroxy-(N-ethyl-2-hydroxy) butyramide prepared above. The reaction mixture was heated to 240° C. for 2 hours. Subsequently the reaction mixture was distilled under reduced pressure yielding γ-hydroxy-propyl oxazoline in approximately 78% yield.

c) Synthesis of γ-hydroxy-(N-ethyl-2-acryloyloxy) butyramide 15 grams of acrylic acid were added to 11 grams of γ-hydroxy-propyl oxazoline slowly at 62° C., bubbling dry air through the liquid, while maintaining the temperature below 90° C. After the addition the reaction temperature was raised to 90° C. and the reaction mixture was stirred for 3 hours at this temperature. After cooling to roomtemperature the reaction mixture was poured into chlorofom, washed thrice with a saturated sodium carbonate solution and once with a saturated sodium chloride solution. After evaporation of the chloroform under reduced pressure γ-hydroxy-(N-ethyl-2-acryloyloxy) butyramide was obtained in approximately 81% yield.

EXAMPLE III

Synthesis of δ-hydroxy-(N-ethyl-2-acryloyloxy) valeramide a) Synthesis of δ-hydroxy-(N-ethyl-2-hydroxy) valeramide 61 grams of ethanol amine were slowly added to 100 grams of valerolactone under nitrogen at 80° C. during which the reaction temperature raised to 120° C. After the addition the reaction temperature was maintained at 120° C. for 2 hours. Subsequent cooling yielded δ-hydroxy-(N-ethyl-2-hydroxy) valeramide in almost quantitative yields.

b) Synthesis of δ-hydroxy-butyl oxazoline 2 ml TBT were added to 161 grams δ-hydroxy-(N-ethyl-2-hydroxy) valeramide prepared above. The reaction mixture was heated to 240° C. for 2 hours. Subsequently the reaction mixture was distilled under reduced pressure yielding δ-hydroxy-butyl oxazoline in approximately 73% yield.

c) Synthesis of δ-hydroxy-(N-ethyl-2-acryloyloxy) valeramide 15 grams of acrylic acid were added slowly at 62° C. to 12 grams of δ-hydroxy-butyl oxazoline, bubbling dry air through the liquid maintaining the temperature below 90° C. After the addition the reaction temperature was raised to 90° C. and the reaction mixture was stirred for 3 hours at this temperature. After cooling to roomtemperature the reaction mixture was poured into chlorofom, washed thrice with a saturated sodium carbonate solution and once with a saturated sodium chloride solution. After evaporation of the chloroform under reduced pressure δ-hydroxy-(N-ethyl-2-acryloyloxy) valeramide was obtained in approximately 79% yield.

EXAMPLE IV

Synthesis of ε-hydroxy-(N-ethyl-2-acryloyloxy) caproamide a) Synthesis of ε-hydroxy-(N-ethyl-2-hydroxy) caproamide 61 grams of ethanol amine were slowly added to 114 grams of caprolactone under nitrogen at 80° C. during which the reaction temperature raised to 120° C. After the addition the reaction temperature was maintained at 120° C. for 2 hours. Subsequent cooling yielded ε-hydroxy-(N-ethyl-2-hydroxy) caproamide in almost quantitative yields.

b) Synthesis of ε-hydroxy-pentyl oxazoline 2 ml TBT were added to 175 grams ε-hydroxy-(N-ethyl-2-hydroxy) caproamide prepared above and the reaction mixture was heated to 240° C. for 2 hours. Subsequently the reaction mixture was distilled under reduced pressure yielding ε-hydroxy-pentyl oxazoline in approximately 77% yield.

c) Synthesis of ε-hydroxy-(N-ethyl-2-acryloyloxy) caproamide 15 grams of acrylic acid were added slowly at 62° C. to 12 grams of ε-hydroxy-pentyl oxazoline while bubbling dry air through the liquid, while maintaining the temperature below 90° C. After the addition the reaction temperature was raised to 90° C. and the reaction mixture was stirred for 3 hours at this temperature. After cooling to roomtemperature the reaction mixture was poured into chlorofom, washed thrice with a saturated sodium carbonate solution and once with a saturated sodium chloride solution. After evaporation of the chloroform under reduced pressure ε-hydroxy-(N-ethyl-2-acryloyloxy) caproamide was obtained in approximately 82% yield.

EXAMPLE V

Synthesis of ε-hydroxy-(N-ethyl-2-acryloyloxy) caproamide a) Synthesis of ε-hydroxy-(N-ethyl-2-hydroxy) caproamide 61 grams of ethanol amine were slowly added to 160 grams of ethyl 6-hydroxy hexanoate under nitrogen at 80° C. during which the reaction temperature raised to 100° C. and the formed ethanol started to distill off. After the addition the reaction temperature was maintained at 100° C. for 6 hours during which the formed ethanol was distilled off. Subsequent cooling yielded ε-hydroxy-(N-ethyl-2-hydroxy) caproamide in almost quantitative yields.

b) Synthesis of ε-hydroxy-pentyl oxazoline To 175 grams ε-hydroxy-(N-ethyl-2-hydroxy) caproamide prepared above were added 2 ml TBT and the reaction mixture was heated to 240° C. for 2 hours. Subsequently the reaction mixture was distilled under reduced pressure yielding ε-hydroxy-pentyl oxazoline in approximately 77% yield.

c) Synthesis of ε-hydroxy-(N-ethyl-2-acryloyloxy) caproamide To 12 grams of ε-hydroxy-pentyl oxazoline 15 grams of acrylic acid were added slowly at 62° C., bubbling dry air through the liquid, , maintaining the temperature below 90° C. After the addition the reaction temperature was raised to 90° C. and the reaction mixture was stirred for 3 hours at this temperature. After cooling to roomtemperature the reaction mixture was poured into chlorofom, washed thrice with a saturated sodium carbonate solution and once with a saturated sodium chloride solution. After evaporation of the chloroform under reduced pressure ε-hydroxy-(N-ethyl-2-acryloyloxy) caproamide was obtained in approximately 81% yield.

EXAMPLE VI

Synthesis of ε-hydroxy-(N-propyl-3-acryloyloxy) caproamide a) Synthesis of ε-hydroxy-(N-propyl-3-hydroxy) caproamide To 114 grams of caprolactone under nitrogen at 80° C. were slowly added 75 grams of 3-amino propanol during which the reaction temperature raised to 120° C. After the addition the reaction temperature was maintained at 120° C. for 2 hours. Subsequent cooling yielded ε-hydroxy-(N-propyl-3-hydroxy) caproamide in almost quantitative yields.

b) Synthesis of ε-hydroxy-(N-propyl-3-acryloyloxy) caproamide To 198 grams ε-hydroxy-(N-propyl-3-hydroxy) caproamide prepared above was slowly added at 90° C. 103 grams of acrylic acid. After stirring at 90° C. for an additional 6 hr the reaction mixture was distilled under reduced pressure yielding ε-hydroxy-(N-propyl-3-acryloyloxy) caproamide in approximately 30%.

EXAMPLE VII

Curing of β-hydroxy-(N-ethyl-2-acryloyloxy) propionamide
20 mg Irgacure 184™ was dissolved in 2 grams of β-hydroxy-(N-ethyl-2-acryloyloxy) propionamide according to Example I. A 10 μm thick film was applied on a gold coated Alumina plate and the film was cured in an Infrared spectrophotometer (Bruker IFS-55) equipped with a 400 W mercury halide lamp. The conversion of acrylate bonds of β-hydroxy-(N-ethyl-2-acryloyloxy) propionamide was monitored in situ during irradiation. The results are shown in Table I.

EXAMPLE VIII

Curing of γ-hydroxy-(N-ethyl-2-acryloyloxy) butyramide
20 mg Irgacure 184™ was dissolved in 2 grams of γ-hydroxy-(N-ethyl-2-acryloyloxy) butyramide according to Example II. A 10 μm thick film was applied on a gold coated Alumina plate and the film was cured in an Infrared spectrophotometer (Bruker IFS-55) equipped with a 400 W mercury halide lamp. The conversion of acrylate bonds of γ-hydroxy-(N-ethyl-2-acryloyloxy) butyramide was monitored in situ during irradiation. The results are shown in Table I.

EXAMPLE IX

Curing of δ-hydroxy-(N-ethyl-2-acryloyloxy) valeramide
20 mg Irgacure 184™ was dissolved in 2 grams of δ-hydroxy-(N-ethyl-2-acryloyloxy) valeramide according to Example III. A 10 μm thick film was applied on a gold coated Alumina plate and the film as cured in an Infrared spectrophotometer (Bruker IFS-55) equipped with a 400 W mercury halide lamp. The conversion of acrylate bonds of δ-hydroxy-(N-ethyl-2-acryloyloxy) valeramide was monitored in situ during irradiation. The results are shown in Table I.

EXAMPLE X

Curing of ε-hydroxy-(N-ethyl-2-acryloyloxy) caproamide
20 mg Irgacure 184™ was dissolved in 2 grams of ε-hydroxy-(N-ethyl-2-acryloyloxy) caproamide according to Example IV. A 10 μm thick film was applied on a gold coated Alumina plate and the film was cured in an Infrared spectrophotometer (Bruker IFS-55) equipped with a 400 W mercury halide lamp. The conversion of acrylate bonds of ε-hydroxy-(N-ethyl-2-acryloyloxy) caproamide was monitored in situ during irradiation. The results are shown in Table I.

EXAMPLE XI

Curing of ε-hydroxy-(N-propyl-3-acryloyloxy) caproamide 20 mg Irgacure 184™ was dissolved in 2 grams of ε-hydroxy-(N-propyl-3-acryloyloxy) caproamide according to Example VI. A 10 μm thick film was applied on a gold coated Alumina plate and the film was cured in an Infrared spectrophotometer (Bruker IFS-55) equipped with a 400 W mercury halide lamp. The conversion of acrylate bonds of ε-hydroxy-(N-propyl-3-acryloyloxy) caproamide was monitored in situ during irradiation. The results are shown in Table I.

Comparative Example A

Curing of hydroxy ethyl acrylate 20 mg Irgacure 184™ was dissolved in 2 grams of hydroxy ethyl acrylate. A 10 μm thick film was prepared on a gold coated Alumina plate and the film was cured in an Infrared spectrophotometer (Bruker IFS-55) equipped with a 400 W mercury halide lamp. The conversion of acrylate bonds of hydroxy ethyl acrylate was monitored in situ during irradiation.

The results of the Examples VII–XI and the Comparative Example A are summarized in Table I.

TABLE I

| Example | rate of double bond conversion (%/sec) |
| --- | --- |
| VII | 161 |
| VIII | 161 |
| IX | 158 |
| X | 153 |
| XI | 150 |
| Comp. Example A | 28 |

These examples demonstrate that the compounds according to the invention result in radiation curable compositions which can be cured at a high cure rate.

What is claimed is:

1. A radiation-curable compound being a mono- or multivalent carboxylic ester obtained by reacting a compound containing a hydroxyalkylamide group and an additional different hydroxy group with an α,β-ethylenically unsaturated carboxylic acid.

2. The radiation-curable compound according to Claim 1, wherein the radiation-curable compound is a compound according to formula (I):

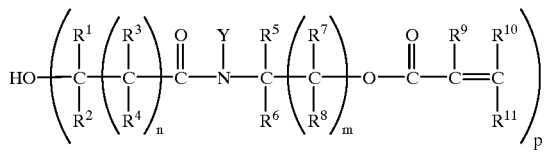

(I)

where:
Y=hydrogen, a $(C_1-C_8)$ alkyl group or

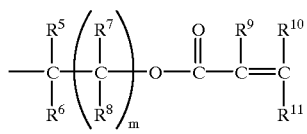

(II)

$R^1$, $R^2$, $R^3$, $R^4$, $R^5$, $R^6$, $R^7$, $R^8$ are, identical or different, hydrogen or a linear, branched or cyclic $(C_1-C_8)$ alkyl chain;

$R^9$=hydrogen, $(C_1-C_5)$ alkyl, —$CH_2OH$ or $CH_2COOX$;

$R^{10}$, $R^{11}$=hydrogen, $(C_1-C_8)$ alkyl, $(C_6-C_{10})$aryl or COOX;

X=hydrogen or $(C_1-C_8)$ alkyl;

n=1–10;

m=1–10; and p=1.

3. A compound according to claim 2, characterized in that Y is hydrogen, $R^1$, $R^2$, $R^3$, $R^4$, $R^5$, $R^6$, $R^7$ and $R^8$ are hydrogen or methyl, $R^9$ is hydrogen or (m)ethyl, $R^{10}$ and $R^{11}$ are hydrogen and m=1–4.

4. A process for the preparation of the compound according to claim 1 by reaction between a hydroxy functional oxazoline and an unsaturated carboxylic acid.

5. A process for the preparation of the compound according to claim 1 by reaction between a hydroxy functional hydroxyalkylamide and an unsaturated carboxylic acid or an unsaturated carboxylic acid chloride, anhydride or ester.

6. A radiation curable composition comprising a compound according to claim 1.

7. A radiation curable coating composition comprising a compound according to claim 1.

8. A coating obtained by radiation curing of a composition according to claim 7.

9. Entirely or partly coated substrate wherein a coating according to claim 8 is applied as the coating.

* * * * *

UNITED STATES PATENT AND TRADEMARK OFFICE
CERTIFICATE OF CORRECTION

PATENT NO.    : 6,437,016 B2
DATED         : August 20, 2002
INVENTOR(S)   : Jansen et al.

It is certified that error appears in the above-identified patent and that said Letters Patent is hereby corrected as shown below:

Title page,
Item [63], Related U.S. Application Data, please correct the filing date of the PCT application to read:
-- Continuation of application No.PCT/NL99/00407, filed on Jun. 30, 1999. --

Signed and Sealed this

Eighth Day of April, 2003

JAMES E. ROGAN
*Director of the United States Patent and Trademark Office*